(12) United States Patent
Ndinguri et al.

(10) Patent No.: US 12,152,089 B2
(45) Date of Patent: *Nov. 26, 2024

(54) LHRH-PLATINUM CONJUGATES FOR TREATING REPRODUCTIVE CANCERS

(71) Applicant: Eastern Kentucky University, Richmond, KY (US)

(72) Inventors: Margaret Ndinguri, Richmond, KY (US); Lindsay Cormier, Richmond, KY (US)

(73) Assignee: Eastern Kentucky University, Richmond, KY (US)

(*) Notice: Subject to any disclaimer, the term of this patent is extended or adjusted under 35 U.S.C. 154(b) by 333 days.

This patent is subject to a terminal disclaimer.

(21) Appl. No.: 17/531,246

(22) Filed: Nov. 19, 2021

(65) Prior Publication Data

US 2022/0193123 A1 Jun. 23, 2022

Related U.S. Application Data

(63) Continuation of application No. 16/159,232, filed on Oct. 12, 2018, now Pat. No. 11,197,888, which is a continuation of application No. 15/367,428, filed on Dec. 2, 2016, now Pat. No. 10,130,717.

(60) Provisional application No. 62/263,350, filed on Dec. 4, 2015.

(51) Int. Cl.
| | |
|---|---|
| *C07K 7/23* | (2006.01) |
| *A61K 33/243* | (2019.01) |
| *A61K 47/64* | (2017.01) |
| *C07F 15/00* | (2006.01) |
| *C07K 19/00* | (2006.01) |

(52) U.S. Cl.
CPC ............ *C07K 7/23* (2013.01); *A61K 33/243* (2019.01); *A61K 47/64* (2017.08); *C07F 15/0093* (2013.01); *C07K 19/00* (2013.01)

(58) Field of Classification Search
None
See application file for complete search history.

(56) References Cited

U.S. PATENT DOCUMENTS

| | | | |
|---|---|---|---|
| 9,221,877 B2 | 12/2015 | Hansel | |
| 10,130,717 B2* | 11/2018 | Ndinguri | ........... A61K 33/243 |
| 11,197,888 B2* | 12/2021 | Ndinguri | ........... C07F 15/0093 |
| 2011/0104074 A1 | 5/2011 | Kakar | |
| 2011/0263500 A1 | 10/2011 | Hansel | |

FOREIGN PATENT DOCUMENTS

WO 2012050892 A2 4/2012

OTHER PUBLICATIONS

Ndinguri et al (Bioconjugate Chem. 2009, 20, 1869-1878) (Year: 2009).*
Arcangeli et al (Obstet Gynecol Int. vol. 2010; Article ID: 486164; Epub Jul. 15, 2010) (Year: 2010).*
Carlson (Oncology Times, vol. 25, Issue 22; p. 36; Nov. 25, 2003) (Year: 2003).*
Ndinguri et al, "Peptide targeting of platinum anti-cancer drugs", Bioconjugate Chem, 2009, pp. 1869-1878, 20(10), American Chemical Society, United States.
Li et al, "Targeted delivery of cisplatin by LHRH-peptide conjugated dextran nanoparticles suppresses breast cancer growth and metastasis", Acta Biomaterialia, 2015, pp. 132-143, 18, Eslevier Ltd, available at http://dx.doi.org/10.1016/j.actbio.2015.02.022.
Aggarwal et al, "[DLys(6)]-luteinizing hormone releasing hormone-curcumin conjugate inhibits pancreatic cancer cell growth in vitro and in vivo", International Journal of Cancer, 2011, pp. 1611-1623, 129(7).
Nukolova et al, "LHRH-Targeted Nanogels as a Delivery System for Cisplatin to Ovarian Cancer", Molecular Pharmaceutics, 2013, 10 (10), pp. 3913-3921.
Ndinguri et al, "Exploring water-soluble Pt(II) complexes of diethylenetriamine derivatives functionalized at the central nitrogen. Synthesis, characterization, and reaction with 5'-GMP", Inorganica Chimica Acta, 2010, 363, pp. 1796-1804.
Wirth et al, "Lectin-mediated drug delivery: influence of mucin on cytoadhesion of plant lectins in vitro", Journal of Controlled Release : official journal of the Controlled Release Society, 2002, 79 (1-3), pp. 183-191.
Mao et al, "EphB2 as a therapeutic antibody drug target for the treatment of colorectal cancer", Cancer Research, 2004, 64 (3), pp. 781-788.
David et al, "Design of a multivalent galactoside ligand for selective targeting of HPMA copolymer-doxorubicin conjugates to human colon cancer cells", Eur J Cancer, 2004, 40 (1), pp. 148-157.
Schally et al, "Cancer chemotherapy based on targeting of cytotoxic peptide conjugates to their receptors on tumors," European Journal of Endocrinology /European Federation of Endocrine Societies, 1999, 141 (1), pp. 1-14.
Dhar et al, "Targeted delivery of cisplatin to prostate cancer cells by aptamer functionalized Pt(IV) prodrug-PLGA-PEG nanoparticles," Proceedings of the National Academy of Sciences of the United States of America, 2008, 105 (45), pp. 17356-17361.
Jamieson et al, "Structure, Recognition, and Processing of Cisplatin-DNA Adducts", Chemical Reviews, 1999, 99 (9), pp. 2467-2498.
Williams, "Clinical significance of esterases in man," Clinical Pharmacokinetics, 1985, 10 (5), pp. 392-403.

(Continued)

*Primary Examiner* — Brian Gangle
*Assistant Examiner* — Andrea K McCollum
(74) *Attorney, Agent, or Firm* — Dinsmore & Shohl LLP

(57) ABSTRACT

The conjugation of luteinizing hormone-releasing hormone (LHRH) with activated cisplatin using a malonate linker gives rise to a new Platinum-LHRH conjugate that effectively targets tumor cells that express the LHRH receptor. The Pt-LHRH conjugate may be used in a method for killing or inhibiting the growth of a tumor cell, especially in late state, highly invasive and aggressive stage IV tumors and in reoccurring tumors.

17 Claims, 11 Drawing Sheets

Specification includes a Sequence Listing.

(56) References Cited

OTHER PUBLICATIONS

Hamelers et al, "Carboplatin nanocapsules: a highly cytotoxic, phospholipid-based formulation of carboplatin," Molecular Cancer Therapeutics, 2006, 5 (8), pp. 2007-2012.
Cubeddu et al, "Efficacy of ondansetron (GR 38032F) and the role of serotonin in cisplatin-induced nausea and vomiting," The New England Journal of Medicine, 1990, 322 (12), pp. 810-816.
Katano et al, "Acquisition of resistance to cisplatin is accompanied by changes in the cellular pharmacology of copper," Cancer Research, 2002, 62 (22), pp. 6559-6565.
Qayum et al, "The effects of gonadotrophin releasing hormone analogues in prostate cancer are mediated through specific tumour receptors," British Journal of Cancer, 1990, 62 (1), pp. 96-99.
Fekete et al, "Characteristics and distribution of receptors for [D-TRP6]-luteinizing hormone-releasing hormone, somatostatin, epidermal growth factor, and sex steroids in 500 biopsy samples of human breast cancer," Journal of Clinical Laboratory Analysis, 1989, 3 (3), pp. 137-147.
Emons et al, "The use of luteinizing hormone releasing hormone agonists and antagonists in gynecological cancers," Hum Reprod, 1994, 9 (7), pp. 1364-1379.
Schally et al, "Cancer chemotherapy based on targeting of cytotoxic peptide conjugates to their receptors on tumors," Eur. J. Endocrinol, 1999, 141 (1), pp. 1-14.
Nagy et al, "Cytotoxic analogs of luteinizing hormone-releasing hormone (LHRH): a new approach to targeted chemotherapy," Drug Future, 2002, 27 (4), pp. 359-370.
Nagy et al, "Targeting cytotoxic conjugates of somatostatin, luteinizing hormone-releasing hormone and bombesin to cancers expressing their receptors: a "smarter" chemotheraphy," Curr. Pharm. Des., 2005, 11 (9), pp. 1167-1180.
Schally et al, "New approaches to treatment of various cancers based on cytotoxic analogs of LHRH, somatostatin and bombesin," Life Sci., 2003, 72 (21), pp. 2305-2320.
Li et al, "Combination of a GnRH agonist with an antagonist prevents flare-up effects and protects primordial ovarian follicles in the rat ovary from cisplatin-induced toxicity: a controlled experimental animal study," Reproductive Biology and Endocrinology : RB&E, 2013, 11, p. 16.
Garcia Garayoa et al, "Chemical and biological characterization of new Re(CO)3/[99mTc](CO)3 bombesin analogues," Nuclear Medicine and Biology 2007, 34 (1), 17-28.
Fischman, et al, "A ticket to ride: peptide radiopharmaceuticals," Journal of nuclear medicine : official publication, Society of Nuclear Medicine, 1993, 34 (12), pp. 2253-2263.
Babich et al, "Technetium-99m-labeled chemotactic peptides: comparison with indium-111-labeled white blood cells for localizing acute bacterial infection in therabbit," Journal of Nuclear Medicine : official publication, Society of Nuclear Medicine, 1993, 34 (12), pp. 2176-2181.
Correia et al, "Radiometallated peptides for molecular imaging and targeted therapy," Dalton Trans, 2011, 40 (23), pp. 6144-6167.
Schibli et al, "Influence of the denticity of ligand systems on the in vitro and in vivo behavior of (99m)Tc(I)-tricarbonyl complexes: a hint for the future functionalization of biomolecules," Bioconjugate Chemistry, 2000, 11 (3), pp. 345-351.
Lazarova et al, "A convenient synthesis, chemical characterization and reactivity of [Re(CO)3(H20)3]Br: the crystal and molecular structure of [Re(CO)3(CH3CN)2Br]," Inorganic Chemistry Communications, 2004, 7 (9), pp. 1023-1026.
Bajusz et al, "Highly potent metallopeptide analogues of luteinizing hormone-releasing hormone," Proceedings of the National Academy of Sciences, USA, 1989, 876 (0027-8424 (Print)), pp. 6313-6317.

Bartholoma et al, "Single amino acid chelates (SAAC): a strategy for the design of technetium and rhenium radiopharmaceuticals," Chem Commun (Camb), 2009, (5), pp. 493-512.
Aggarwal et al, "Inhibition of growth and survival of human head and neck squamous cell carcinoma cells by curcumin via modulation of nuclear factor-KB signaling," International Journal of Cancer, 2004, 111 (5), pp. 679-692.
Leuschner et al, "Human prostate cancer cells and xenografts are targeted and destroyed through luteinizing hormone releasing hormone receptors," The Prostate, 2003, 56 (4), 239-49.
Yang et al, "Technetium-99m-labeled Arg-Gly-Asp-conjugated alpha-melanocyte stimulating hormone hybrid peptides for human melanoma imaging," Nuclear Medicine and Biology, 2010, 37 (8), 873-83.
Taheri, "The in-vivo antitumor," International Journal of Pharmaceutics (2012).
Schally et al, "Peptide analogs in therapy of prostate cancer," Prostate (2000), 45, pp. 158-166.
Miller, "Growth of human breast cells inhibited by a luteinizing hormone-releasing hormone agonist," Nature, 1985, 313, pp. 231-233.
Szepashzi et al, "Effective Treatment of advanced estrogen-independent MXT mouse mammary cancers with targeted cytotoxic LHRH analogs," Breast Cancer Res. Treat., 1999, 56, pp. 267-276.
Berners-Price et al, "Hydroloysis products of cisplatin: pKa determinations via [1H, 15N] NMR spectroscopy," Journal of the Chemical Society, Chemical Communications, 1992, pp. 789-791.
Appleton et al, "NMR study of acid-base equilibria and other reactions of ammineplatinum complexes with aqua and hydroxo ligands," Inorganic Chemistry, 1989, 28 pp. 1989-1993.
Scalici et al, "Imaging VCAM-1 as an indicator of treatment efficacy in metastatic ovarian cancer," J. Nucl. Med., 2013, 54(11), pp. 1883-1889.
Das et al, "Squalene selectivity protects mouse bone marrow progenitors against cisplatin and carboplatin-induced cytotoxicity in vivo without protecting tumor growth," Neoplasia, 2008, 10(10), pp. 1105-1119.
Karginova et al, "Efficacy of carboplatin alone and in combination with ABT888 in intracranial murine models of BRCA-mutated and BRCA-wild-type triple-negative breast cancer," Molecular Cancer Therapeutics, 2015, 14(4), pp. 920-930.
Li, "Preclinical relevance of dosing time for the therapeutic index of gemcitabine-cisplatin," British Journal of Cancer, 2005, 92(9), pp. 1684-1689.
Arcangeli et al, "The LH/hCG Axis in Endometrial Cancer: A New Target in the Treatment of Recurrent or Metastatic Disease", Obstet Gynecol Int vol. 2010(8); Article ID: 486164; Epub Jul. 15, 2010, Year: 2010.
Skolnick et al, "From genes to protein structure and function: novel applications of computational approaches in the genomic era", Trends Biotechnol, Jan. 2000, 18(1);34-9, Year: 2000.
Burgess et al, "Possible dissociation of the heparin-binding and mitogenic activities of heparin-binding (acidic fibroblast) growth factor-1 from its receptor-binding activities by site-directed mutagenesis of a single lysine residue", J Cell Biol 111:2129-2138, 1990, Year: 1990.
Lazar et al, "Transforming growth factor alpha: mutation of aspartic acid 47 and leucine 48 results in different biological activities", Mol Cell Biol, 8:1247-1252, 1988, Year: 1988.
Miosge, "Comparison of predicted and actual consequences of missense mutations", Proc Natl Acad Sci USA, Sep. 15, 2015, 112(37):E5189-98, Year: 2015.

* cited by examiner

LHRH-PLATINUM CONJUGATES FOR TREATING REPRODUCTIVE CANCERS

CROSS-REFERENCE TO RELATED APPLICATIONS

This application is a continuation of U.S. patent application Ser. No. 16/159,232 filed Oct. 12, 2018, which is a continuation of U.S. patent application Ser. No. 15/367,428 filed Dec. 2, 2016, the disclosures of which are incorporated herein by reference. U.S. patent application Ser. No. 16/159,232 and U.S. patent application Ser. No. 15/367,428 both claim the benefit of U.S. Provisional Application No. 62/263,350, filed Dec. 4, 2015, the disclosure of which is also incorporated herein by reference.

STATEMENT REGARDING FEDERALLY SPONSORED RESEARCH AND DEVELOPMENT

This invention was made with government support under Award Number P20GM103436 awarded by the National Institute of Health. The government has certain rights in the invention.

FIELD OF THE DISCLOSURE

The present invention relates to treating and preventing cancers, more particularly to Platinum (Pt)-LHRH conjugates for treating reproductive cancers that allows for the effective delivery of cytotoxic drugs in the platinum family to a tumor cell.

DISCUSSION OF RELATED ART

Prostate and breast cancer are some of the most common cancers among individuals in the United States. Although the incidence of prostate cancer is markedly age dependent and about two-fold higher in African-Americans than Caucasians, prostate cancer is one of the leading causes of cancer deaths among men of all races. Conventional chemotherapeutic approaches yield median overall survival rates for stage IV prostate of only twenty-nine percent (29%) and stage IV breast cancer of only twenty-three percent (23%). Despite recent advances in the first-line treatment of both cancer types, many patients eventually relapse; their tumors become chemo resistant; leading to patient mortality. One of the problems in cancer chemotherapy is the deleterious side effects of anticancer drugs designed to destroy rapidly dividing cells, including cells found in healthy tissues. Due to these severe side effects, doctors often resort to dose reduction, treatment delay or discontinuance of therapy.

Cisplatin and carboplatin are two known chemotherapeutic drugs in the platinum (Pt) family of anticancer drugs. They are the most potent drugs in the Pt family and are commonly given in late state or stage IV cancer types as they effectively disrupt cell cycle/cellular division and can cause cancer cells cytotoxicity/apoptosis leading to tumor death or reduction in size. Cisplatin inhibits growth of tumor cells by interference with normal transcription and DNA replication mechanisms leading to eventual cell death. Cisplatin chemotherapy, however, is not currently very effective in prostate cancer treatment due to its poor targeting of tumor cells and the development of chemo resistant tumors. Carboplatin, an analog of cisplatin, has gained greater use because of its decreased nonspecific toxicity and its activity against cisplatin-resistant tumors. See I. Hamelers, et al., "Carboplatin nanocapsules: a highly cytotoxic, phospholipid-based formulation of carboplatin," Molecular Cancer Therapeutics 2006, 5 (8), (2007-12).

Due to their lack of selectivity towards cancer cells the high doses administered to a patient to reach a therapeutic response for both carboplatin and cisplatin cause severe side effects including: nausea, vomiting, taste changes, hair loss, weakness, abdominal pain, diarrhea, mouth sore, infection, peripheral neuropathy, central neurotoxicity hearing loss, abnormal blood electrolyte levels, abnormal liver enzyme levels, cardiovascular events, dizziness, fatigue, etc. See L. X. Cubeddu, et al., "Efficacy of ondansetron (GR 38032F) and the role of serotonin in cisplatin-induced nausea and vomiting," The New England Journal Of Medicine, 322 (12), pp. 810-6 (1990). Additionally, certain cancers can develop resistance to cisplatin via efflux pumps. See K. Katano, et al., "Acquisition of resistance to cisplatin is accompanied by changes in the cellular pharmacology of copper," Cancer Research, 62 (22), pp. 6559-65 (2002). Despite the current lack of effective chemotherapies utilizing cisplatin, the drug remains attractive for development in cancer treatments due to its potency. Accordingly, the development of treatment methods and chemotherapies that will better direct cisplatin to its desired target, tumor cells, with fewer side effects and improved efficacy is needed.

Various studies have found that receptors for certain peptides/hormones are found in higher concentration in tumor cells than in normal cells. For example, the receptor for luteinizing hormone releasing hormone (LHRH) is overexpressed in numerous types of cancer cells including but not limited to reproductive cancers including breast, ovarian, and prostate cancers. See A. Taheri, "The in-vivo antitumor," International Journal of Pharmaceutics, (2012). Various non-reproductive cancers have been shown to overexpress the LHRH receptor as well, including but not limited to: lung, bladder, and pancreatic cancers, among others. LHRH, also referred to as gonadotropin releasing hormone (GnRH), is a decapeptide regulatory hormone comprised of SEQ ID NO 1 pGlu-His-Trp-Ser-Tyr-Gly-Leu-Arg-Pro-Gly-NH2 involved in reproduction. Studies have shown that LHRH receptors are overexpressed in breast, prostate, endometrial and ovarian cancers, along with non-reproductive cancers, in comparison to normal cells, making the LHRH peptide a good candidate for drug targeting. See A. Qayum, et al., "The effects of gonadotrophin releasing hormone analogues in prostate cancer are mediated through specific tumour receptors," See British Journal Of Cancer, 62 (1), pp. 96-9 (1990); M. Fekete, et al., "Characteristics and distribution of receptors for [D-TRP6]-luteinizing hormone-releasing hormone, somatostatin, epidermal growth factor, and sex steroids in 500 biopsy samples of human breast cancer," Journal Of Clinical Laboratory Analysis, 3 (3), pp. 137-47 (1989); G. Emons, et al., "The use of luteinizing hormone releasing hormone agonists and antagonists in gynecological cancers," Hum Reprod, 9 (7), pp. 1364-79, (1994).

Additionally, LHRH has been shown to be effective as a stand-alone treatment in certain cancer cases. Specific analogs of LHRH peptide for use in targeting LHRH receptors in prostate and breast cancers are also known in the art. See A. V. Schally, et al., "Peptide analogs in the therapy of prostate cancer," Prostate, 45, pp. 158-66 (2000); W. R. Miller, "Growth of human breast cancer cells inhibited by a luteinizing hormone-releasing hormone agonist," Nature, 313, pp. 231-33 (1985); K. Szepashzi, et al., "Effective treatment of advanced estrogen-independent MXT mouse mammary cancers with targeted cytotoxic LHRH analogs," Breast Cancer Res. Treat., 56, pp. 267-76 (1999).

Existing methods for using hormones (such as LHRH and its analogs), peptides, antibodies and ligands to specifically target and direct anticancer drugs and compounds to cancer cells via receptor binding sites on those cells continue to be explored in field of biomedical pharmacology with limited success. See Aggarwal, et al., "[DLys(6)]-luteinizing hormone releasing hormone-curcumin conjugate inhibits pancreatic cancer cell growth in vitro and in vivo" International Journal of Cancer 2011, 129 (7), 1611-23; M. Wirth, et al., "Lectin-mediated drug delivery: influence of mucin on cytoadhesion of plant lectins in vitro," Journal Of Controlled Release: Official Journal Of The Controlled Release Society, 79 (1-3), pp. 183-91 (2002); W. Mao, et al., "EphB2 as a therapeutic antibody drug target for the treatment of colorectal cancer," Cancer Research, 64 (3), pp. 781-8 (2004); A. David, et al., "Design of a multivalent galactoside ligand for selective targeting of HPMA copolymer-doxorubicin conjugates to human colon cancer cells," Eur J Cancer, 40 (1), pp. 148-57 (2004); A. V. Schally, et al., "Cancer chemotherapy based on targeting of cytotoxic peptide conjugates to their receptors on tumors," European Journal Of Endocrinology/European Federation of Endocrine Societies, 141 (1), pp. 1-14 (1999); and U.S. Pat. No. 9,221,877

The delivery of cisplatin by LHRH has been explored by the use of nanogels. However, the direct linkage of LHRH to cisplatin as a method of delivery has not been developed. The use of nanogels employs a more complex methodology involving cisplatin incorporation and release from the nanogel. Rendering it a less effective mode of delivery. See N. Nukolova, et al., "LHRH-Targeted Nanogels as a Delivery System for Cisplatin to Ovarian Cancer," Mol. Pharmaceutics, 10 (10), pp. 3913-3921 (2013);

Therefore, there is a need for Platinum (Pt)-LHRH conjugates for treating reproductive cancers that allows for the effective delivery of cytotoxic drugs in the platinum family to tumor cells. Such a needed Platinum (Pt)-LHRH conjugates would decrease adverse side effects associated with existing drugs, and limit nonspecific activity.

SUMMARY OF THE DISCLOSURE

The present invention describes the conjugation of luteinizing hormone-releasing hormone ([DLys$^6$]-LHRH) with activated cisplatin using a malonate linker that gives rise to new Platinum (Pt)-LHRH conjugate that effectively targets tumor cells that express the LHRH receptor. The present embodiment overcomes the existing shortcomings in this area by accomplishing these critical objectives. The Pt-LHRH conjugate is intended to be used in the treatment of reproductive and non-reproductive cancers expressing the LHRH receptor. The use of the novel Pt-LHRH conjugate will increase the concentration of the platinum anticancer drug in tumor cells and attenuate unnecessary exposure to normal cells. The new Pt-LHRH targeted anticancer drug has applications to prostate cancer and other metastatic cancers expressing the LHRH receptor such as breast, melanoma, lung and pancreatic cancers, especially in late stage, highly invasive and aggressive stage IV tumors, and in reoccurring tumors as these are the most difficult to treat.

Other features and advantages of the present invention will become apparent from the following more detailed description, taken in conjunction with the accompanying drawings, which illustrate, by way of example, the principles of the invention.

DETAILED DESCRIPTION OF THE PREFERRED EMBODIMENT

Figure 1:
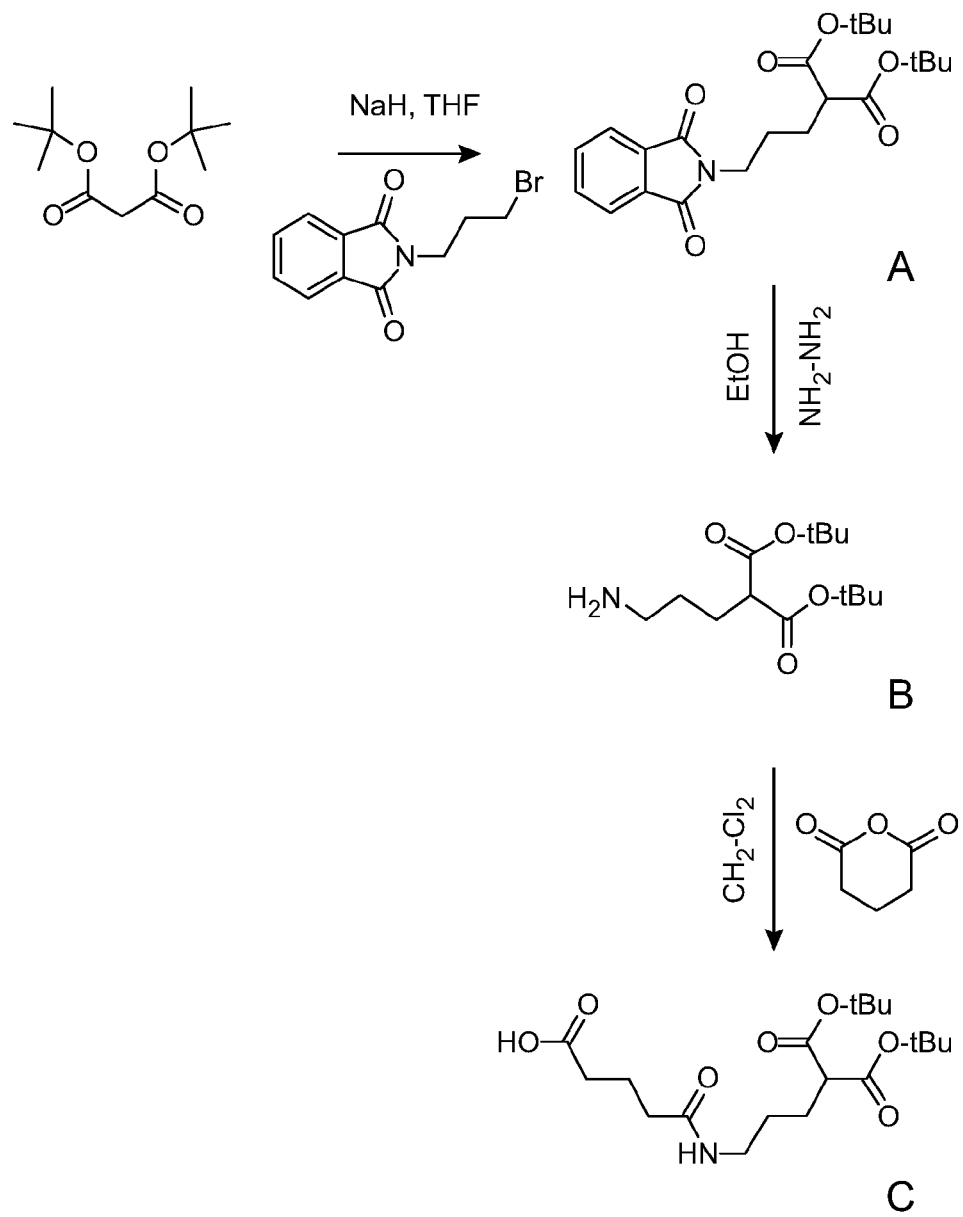
FIG. 1 depicts a synthesis of a malonate (mal) linker in accordance with a preferred embodiment of the present invention.

In the following discussion that addresses a number of embodiments and applications of the present invention, reference is made to the accompanying drawings that form a part hereof, and show by way of illustration specific embodiments in which the invention may be practiced. It is to be understood that other embodiments may be utilized and changes may be made without departing from the scope of the present invention.

Various inventive features are described below that can be used independently of one another or in combination with other features. However, any single inventive feature may not address any of the problems discussed above or only address one of the problems discussed above. Further, one or more of the problems discussed above may not be fully addressed by any of the features described below.

As used herein, the singular forms "a", "an" and "the" include plural referents unless the context clearly dictates otherwise. "And" as used herein is interchangeably used with "or" unless expressly stated otherwise. As used herein, the term 'about" means +/−5% of the recited parameter. All embodiments of any aspect of the invention can be used in combination, unless the context clearly dictates otherwise.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "wherein", "whereas", "above," and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

The present invention provides a compound and a method for generating new Platinum (Pt)-LHRH conjugate which will allow for the effective delivery of cytotoxic drugs in the platinum family to treat tumor cells with decreased adverse side effects associated with existing drugs, and limit nonselective activity. In a preferred embodiment, LHRH is conjugated to activated cisplatin using a malonate (mal) linker on [DLys6]-LHRH. The attachment of the mal linker on position 6 of the LHRH ensures that the intrinsic properties of the LHRH peptide are maintained. In the preferred embodiment, an ester bond is introduced between the components of the conjugate. Existing published reports have shown that such a bond is hydrolyzed by cellular esterase, leaving the drug free to act at the cellular level. See Aggarwal, et al., "[DLys(6)]-luteinizing hormone releasing hormone-curcumin conjugate inhibits pancreatic cancer cell growth in vitro and in vivo" International Journal of Cancer 2011, 129 (7), 1611-23; U. S. Pat No: 0263500A1.

Figure 14:
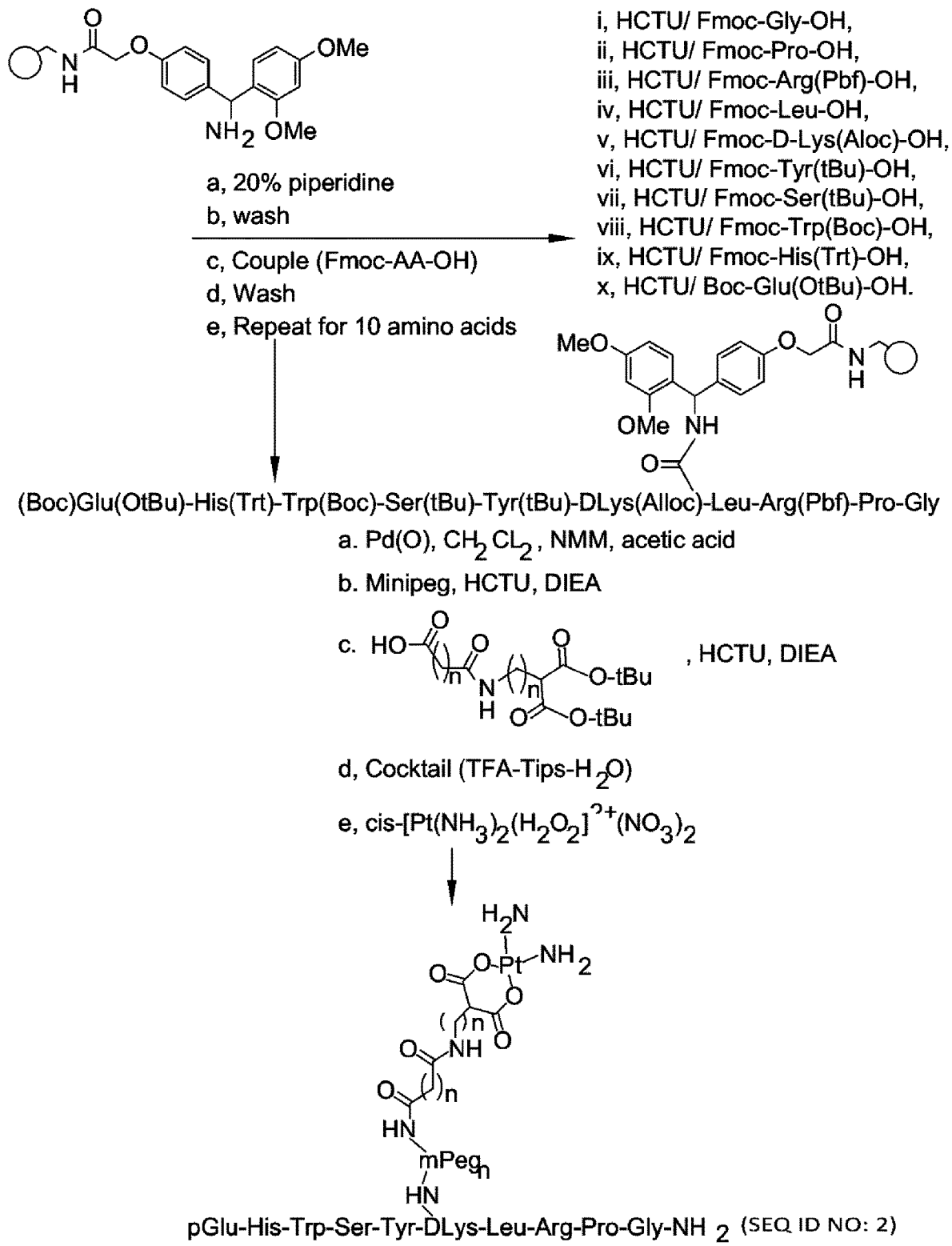
FIG. 14 depicts the conjugation of SEQ ID NO 2 with activated cisplatin using a malonate linker with variation in linker length that gives rise to Pt-n-LHRH.

In the preferred embodiment, LHRH is conjugated to activated cisplatin using the mal linker without the additional use of Polyethylene glycol (PEG) groups or chains, ligands, peptides, hormones, or other linkers. The addition of a PEG group to a linker is known to provide synthetic compound solubility or enhance bioavailability. In the preferred embodiment, the Pt-LHRH conjugate does not require a PEGylated linker to be soluble and effective. Alternatively, in a further embodiment, the Pt-LHRH conjugate may incorporate a PEGylated linker to enhance solubility (see FIG. 14). PEGylation has been employed during nanoparticle and NGR-Pt formulation. See M. Ndinguri, et al., "Peptide targeting of platinum anti-cancer drugs," Bioconjugate Chem., 20, pp. 1869-78 (2009); N. Nukolova, "LHRH-targeted nanogels as delivery system for cisplatin to ovarian cancer," Mol. Pharmaceutical, 10 (10), pp. 3913-21 (2013); U.S. Patent Application No. 2011/0104074 A1.

In addition, surprisingly binding of unaltered cisplatin is unfavorable and activated cisplatin which was found to be needed for binding to the mal-LHRH moiety. Further, the Pt-LHRH is highly soluble and has not been shown to precipitate out of solution even after four months of storage in a 10 mM solution at 4° C. This could aid in therapeutic administration of the compound.

Figure 2:
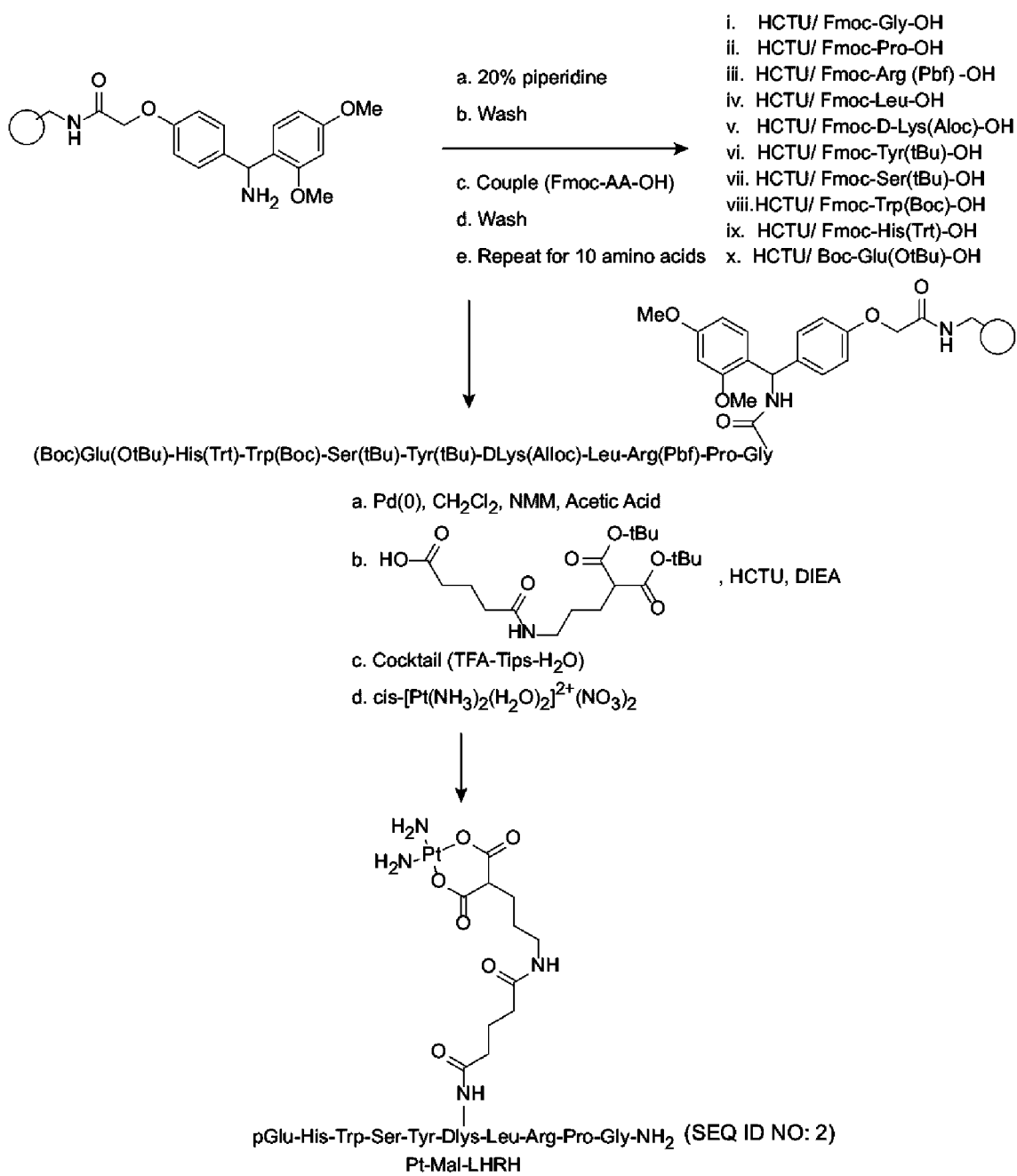
FIG. 2 depicts the conjugation of SEQ ID NO 2 with activated cisplatin using a malonate linker that gives rise to Pt-LHRH.
Figure 13:
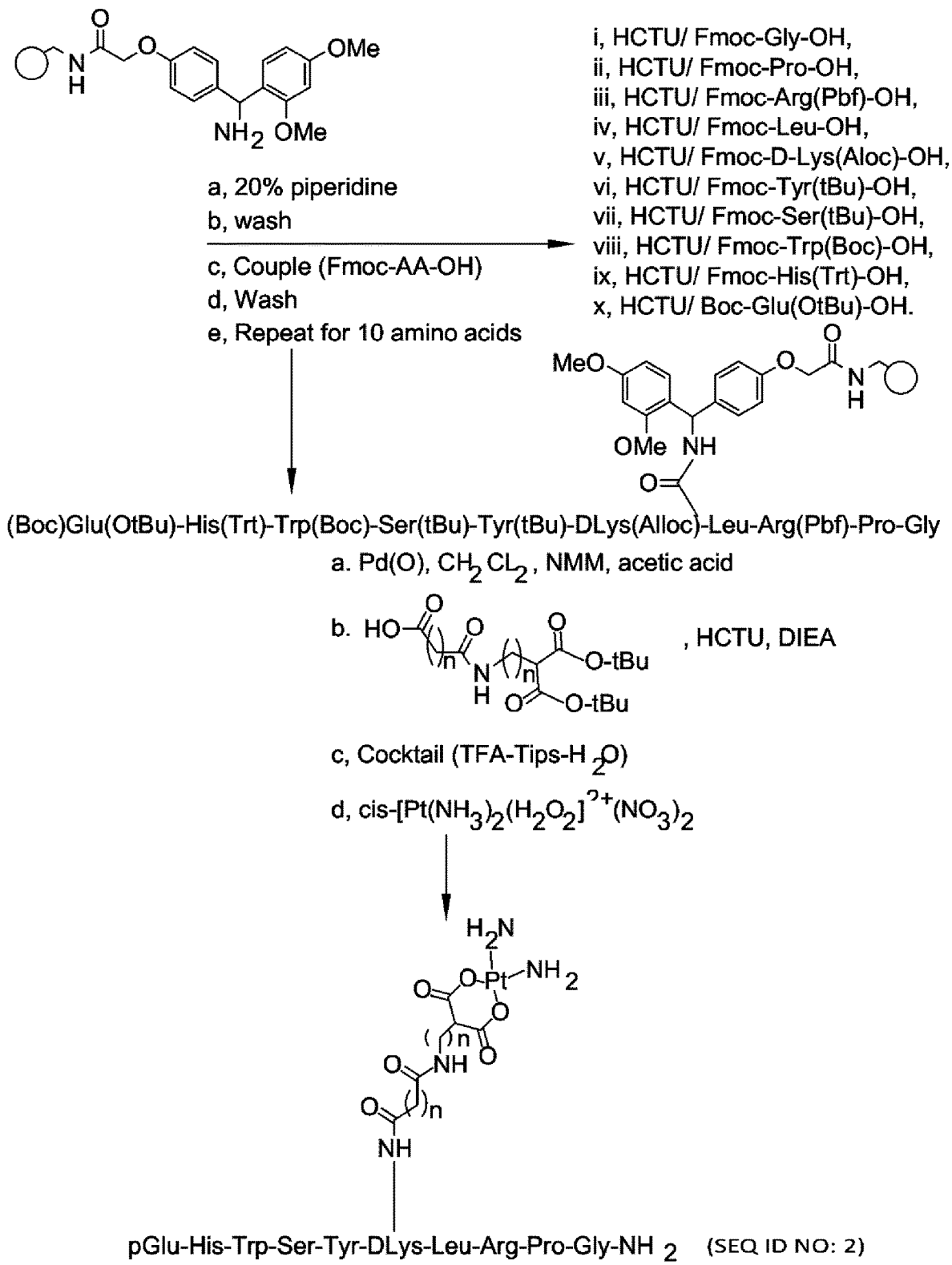
FIG. 13 depicts the conjugation of SEQ ID NO 2 with activated cisplatin using a malonate linker in a PEGylated state that gives rise to Pt-Peg-LHRH.

The present invention describes the use of Boc protecting group instead of Fmoc in the last amino acid (Boc-Glu (OtBu) (see. FIG. 2). This allows for a straight forward synthesis because it reduces the number of synthetic steps and avoids unwanted side chain reactions that can occur at the glutamic acid position. The acid labile Boc protecting group is conveniently removed at the end during cleavage of the peptide from the resin. The activated cisplatin is used to bind to the mal-LHRH moiety. The malonate linker chelates platinum in a similar manner to carboplatin, even with variations in linker length, as shown in FIG. 13. As shown in FIG. 13, additional carbons may be added to the malonate linker without altering the desired functionality or effect of Pt-LHRH. The end compound (see FIG. 2) chemically resembles carboplatin. Hence, carboplatin is utilized for treatment comparison. The Pt-LHRH has more effective systemic distribution and bioavailability to carboplatin. In addition, the cellular internalized into the cancer cell following its Pt-LHRH is cleaved by proteases which produces a platinum complex that resembles cisplatin in structure and function.

In one embodiment, the mal linker may be utilized in combination with PEG groups, ligands, peptides, hormones, or other linkers.

In one embodiment, cisplatin may be substituted with any other cytotoxic drug in the platinum family or any known derivatives thereof.

In one embodiment, aliphatic linkers other than the mal linker may be used, either alone or in combination with other linkers.

Finally, in yet another embodiment, the targeting peptide can be endogenous LHRH or an analog thereof, including but not limited to, [D-Trp6]-LHRH, [D-Ala6]-LHRH, [Gln8]-LHRH, luteinizing hormone, chorionic gonadotropin, antide, gonadorelin, leuprolide, leuprorelin, histerlin, buserelin, triptorelin, and fragmented portions containing a binding moiety. In addition, analogs for LHRH, including LHRH receptor agonists and antagonists may be used in alternate embodiments. See A. V. Schally, et al., "Peptide analogs in the therapy of prostate cancer," Prostate, 45, pp. 158-66 (2000); W. R. Miller, "Growth of human breast cancer cells inhibited by a luteinizing hormone-releasing hormone agonist," Nature, 313, pp. 231-33 (1985); K. Szepashzi, et al., "Effective treatment of advanced estrogen-independent MXT mouse mammary cancers with targeted cytotoxic LH-RH analogs," Breast Cancer Res. Treat., 56, pp. 267-76 (1999).

The novel Pt-LHRH conjugate is intended to be used in the treatment of reproductive and non-reproductive cancers expressing the LHRH receptor. The use of the novel Pt-LHRH conjugate will increase the concentration of the platinum anticancer drug in tumor cells and attenuate unnecessary exposure to normal cells. The new Pt-LHRH targeted anticancer drug has applications to prostate cancer and other metastatic cancers such as breast, melanoma, lung and pancreatic cancers, especially in late stage, highly invasive and aggressive stage IV tumors, and in reoccurring tumors as these are the most difficult to treat.

In one embodiment the Pt-LHRH conjugate targets and binds to the LHRH receptors of any cancer cell or any tumor microenvironment that expresses these receptors. Moreover, protease produced by the tumor cells effectively cleave the linker to release the "warhead," i.e., cisplatin, carboplatin, or other platinum drug or derivative, and thereby to achieve more effective concentrations of the therapeutic agents in the targeted area. Further, the targeted Pt-LHRH conjugate will selectively kill tumor cells and prevent or reduce dose-limiting systemic toxicity of said chemotherapeutic drugs.

The following examples illustrate the innovation and significance of using Pt-LHRH are discussed in studies involving prostate and breast cancer, however, the applications of, mechanisms of action and/or relevance of Pt-LHRH are not restrictive to treatment of those cancers.

Example 1

FIG. 1 depicts the synthesis of Mal Linker for conjugation with the LHRH Peptide and cisplatin in accordance with a preferred embodiment of the present invention. In the preferred example, the mal linker was successfully prepared by alkylating di-tert-butyl malonate using bromopropylphtalimide using a strong base under absolute dry conditions (see FIG. 1(A)). The product obtained, di-tert-butyl 2-(3-phthalimidopropyl) malonate was isolated using silica column chromatography and deprotected using hydrazine in absolute ethanol to give a free primary amine end (see FIG. 1(B)). The primary amine was reacted with gluatric anhydride to give di-tert-butyl 2-(3-(4-Carboxybutanamido)propyl)-malonate (Mal) (see FIG. 1(C)) as described by M. Ndinguri, et al., Bioconjugate Chem., 20, pp. 1869-78 (2009) thereby introducing a carboxylic functional group which was attached to the peptide moiety. Each step was purified by column chromatography or extraction and dried before proceeding to the next step.

Example 2

FIG. 2 depicts a synthesis of Pt-LHRH conjugate in accordance with a preferred embodiment of the present invention. The Mal-LHRH decapeptide was synthesized using Fmoc solid phase chemistry techniques and then chelated to activated cisplatin. Fmoc-Rink Amide-AM resin was placed onto a reaction vessel and washed with DMF and DCM in continuous-flow mode using a PS3 peptide synthesizer. The side chain protected amino acids derivatives used were Fmoc-Gly-OH, Fmoc-Pro-OH, Fmoc-Arg(Pbf)-OH, Fmoc-Leu-OH, Fmoc-DLys(Aloc)-OH, Fmoc-Tyr(tBu)-OH, Fmoc-Ser(tBu)-OH, Fmoc-Trp(Boc)-OH, Fmoc-His(Trt)-OH and Boc-Glu(OtBu)-OH. Moreover, the use of Boc protecting group instead of Fmoc in the last amino acid (Boc-Glu(OtBu)) allows for a straightforward synthesis because it reduces the number of synthetic steps and avoids unwanted side chain reactions. The acid labile Boc protecting group is conveniently removed in the end during cleavage of the peptide from the resin. The amino acid couplings employed four equivalents of amino acid and (2-(6-Chloro-1 H-benzotriazole-1-yl)-1, 1,3,3-tetramethylaminium hexafluorophosphate (HCTU) and sometimes (7-Azabenzotriazol-1-yloxy) tripyrrolidinophosphoniumhexafluorophosphate (PyAOP) or other known coupling reagents dissolved in 0.4 M N-methylmorpholine (NMM) in DMF at room temperature. The allyloxycarbonyl (aloc) protecting group on the D-lys was selectively removed using palladium. The amine end of the D-lys was coupled with the mal linker (see FIG. 2) and the conjugate cleaved from the resin using TFA-Tips-H2O-Phenol or TFA-Tips-H2O or TFA-Thioanisole-H2O or TFA-Thioanisole-H2O cocktail to yield of LHRH-mal. Activated cisplatin was formed using cisplatin, silver nitrate and water in accordance with known methods as described in Berners-Price, et al., "Hydrolysis products of cisplatin: pKa determinations via [1H, 15N] NMR spectroscopy," Journal of the Chemical Society, Chemical Communications (1992) 789-791; Appleton et al., "NMR study of acid-base equilibria and other reactions of ammineplatinum complexes with aqua and hydroxo ligands," Inorganic Chemistry, (1989) 28, 1989-1993. Reaction of LHRH-mal and activated cisplatin yielded Pt-LHRH. Conjugation of Pt to LHRH yields a structure similar to carboplatin no matter the malonate linker carbon chain length (see FIG. 13) nor the PEGylation state (see FIG. 14).

Figure 3:
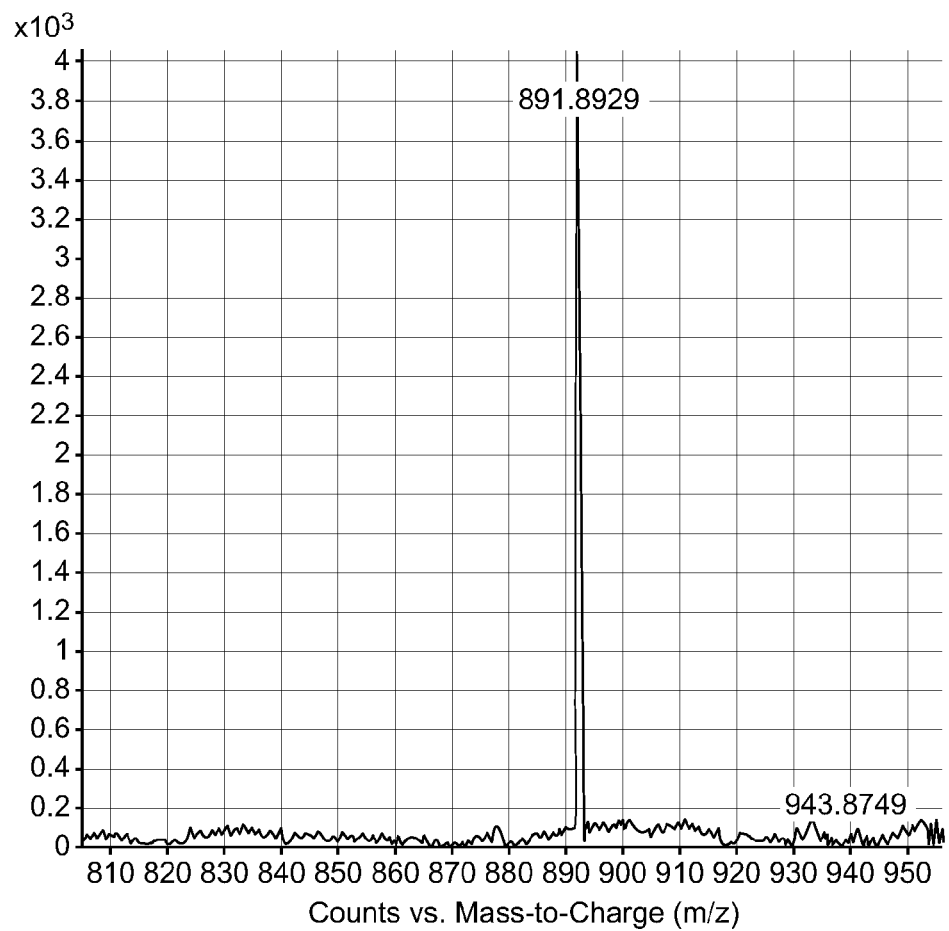
FIG. 3 depicts a mass spectrum of Pt-LHRH conjugate in accordance with the preferred embodiment of the present invention.

FIG. 3 depicts a mass spectrum of Pt-LHRH conjugate in accordance with a preferred embodiment of the present invention.

Example 3

Cytotoxicity Assay, in-vitro assays were used to explore the role of Pt-LHRH conjugates in cytotoxicity. The cytotoxic effect of free carboplatin, free LHRH and Pt-LHRH conjugate were assayed and compared using methyl thiazol tetrazolium (MTT) (3-(4,5-dimethylthiazol-2-yl)-2,5diphenyltetrazolium bromide) assay as described in S. Aggarwal, et al., "Inhibition of growth and survival of human head and neck squamous cell carcinoma cells by curcumin via modulation of nuclear factor-KB signaling," International Journal of Cancer, 111 (5), pp. 679-92 (2004).

Figure 4:
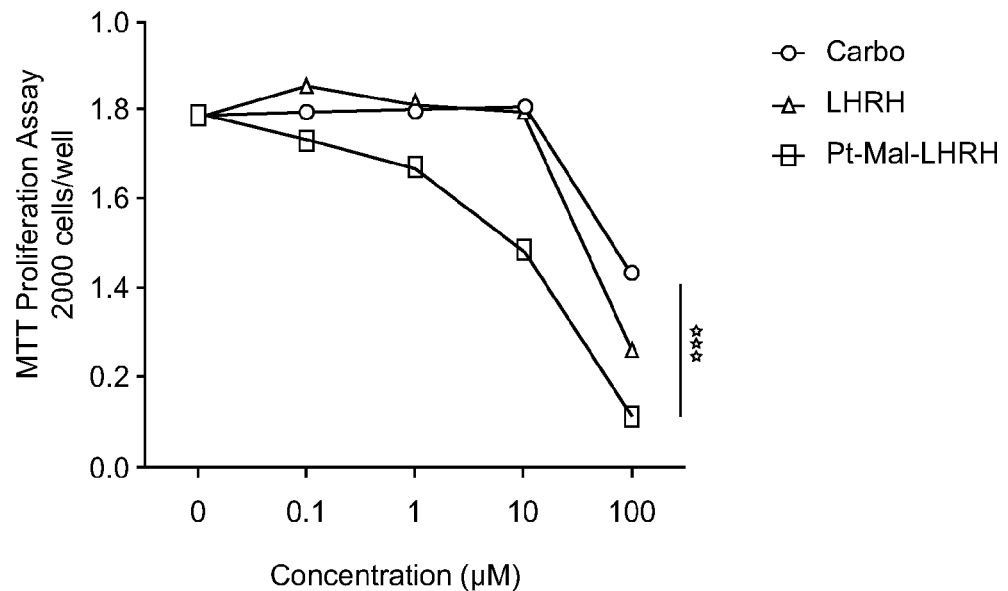
FIG. 4 depicts a cytotoxicity of carboplatin, LHRH and Pt-LHRH against prostate cancer cells in an methyl thiazol tetrazolium (MTT) proliferation assay in accordance with the preferred embodiment of the present invention.
Figure 5:
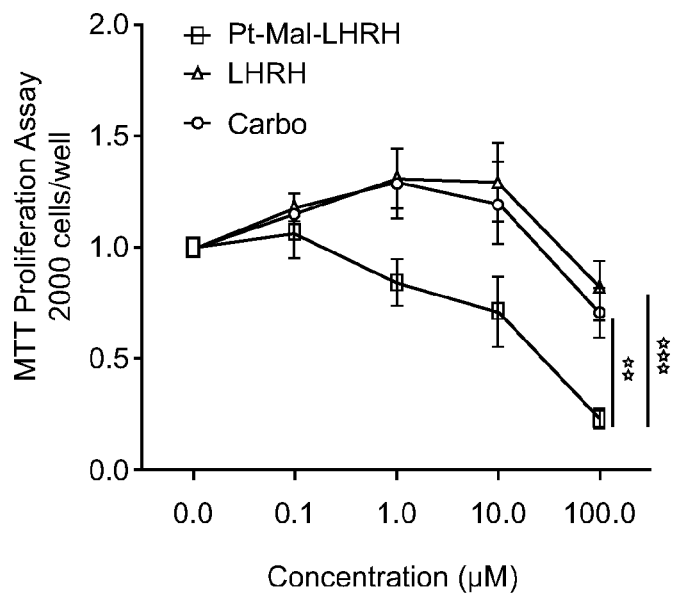
FIG. 5 depicts a cytotoxicity of carboplatin, LHRH and Pt-LHRH against breast cancer cells in an MTT proliferation assay in accordance with the preferred embodiment of the present invention.

Cells from prostate cancer cell line PC-3 (CRL-1435) and breast cancer cell line 4T1 (CRL-2539) were obtained from American Culture Type Collection (ATCC) and cultured in DMEM supplemented with 10% FBS, 100 units/mL penicillin, and 100 µg/mL streptomycin. Two thousand cells of PC-3 or 4T1 were treated with various concentrations of free carboplatin, LHRH or Pt-LHRH for 24 hours followed by further incubation (no treatment) for 48 hours. The results were assayed using MTT (3-(4,5-dimethylthiazol-2-yl)-2,5-diphenyltetrazolium bromide) assay. Pt-LHRH showed a significant increase in cytotoxicity compared to carboplatin in both cell lines. As shown in FIG. 4 and FIG. 5, stage IV prostate and breast cancer cells showed a significant decrease in cancer cell proliferation/viability compared to carboplatin alone.

Figure 6:
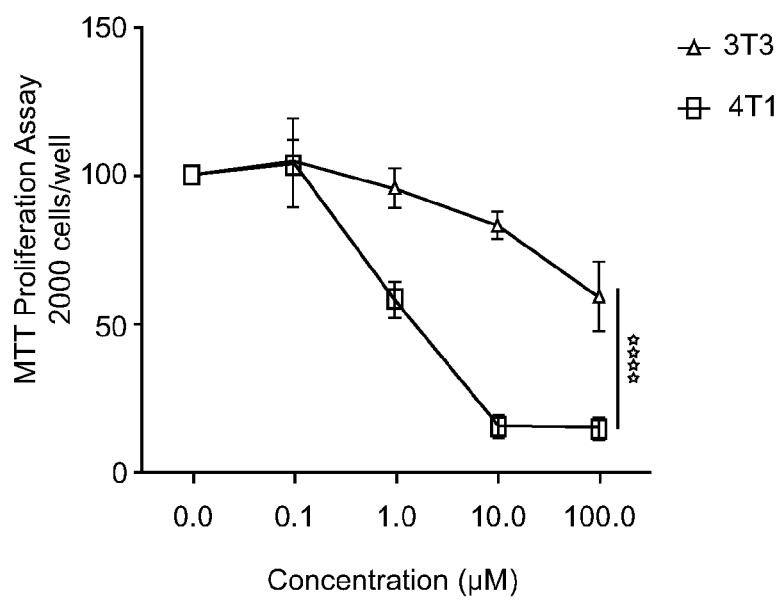
FIG. 6 depicts a the cytotoxicity of Pt-LHRH against breast cancer cells and normal mammary cells in an MTT proliferation assay in accordance with the preferred embodiment of the present invention.

As shown in FIG. 6, Pt-LHRH attenuates 4T1 breast cancer cell viability compared to normal mammary cells (3T3). The 3T3 cells were obtained from ATCC (CRL-2752) were treated with Pt-LHRH from a range of 0.1 µM to 100 µM. The viability rates were analyzed by a MTT assay as previously described. As shown in FIG. 6, there was a significant decrease in normal mammary cell cytotoxicity compared to 4T1 cancer cells when treated with Pt-LHRH. These results indicate that the targeting activity of Pt-LHRH is effective and suggest that there may be less deleterious side effects from treatment with Pt-LHRH as reported from cisplatin or carboplatin alone.

Example 4

Drug Uptake Measurements

Figure 7:
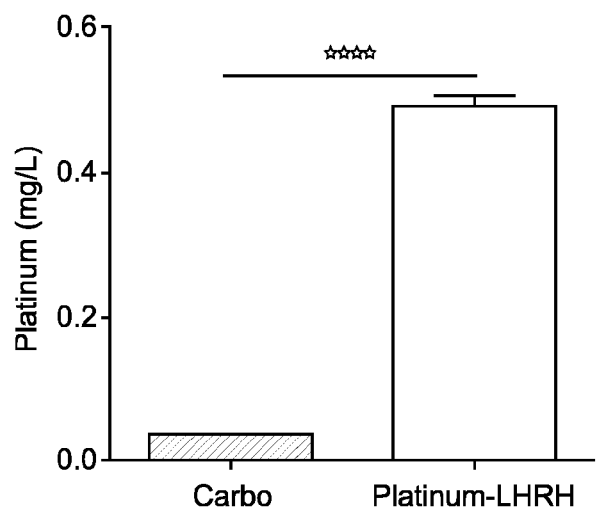
FIG. 7 compares drug uptake activity in breast cancer cells treated with carboplatin and Pt-LHRH in accordance with the preferred embodiment of the present invention.

4T1 Breast Cancer cells were treated with a 100 µM concentration carboplatin or Pt-LHRH for 24 hours. The collected samples were lysed with nitric acid and analyzed for the presence of platinum using inductive coupled plasma (ICP-OES). As shown in FIG. 7, there was a significant increase in uptake (20 fold) of Pt-LHRH compared to carboplatin.

Figure 8:
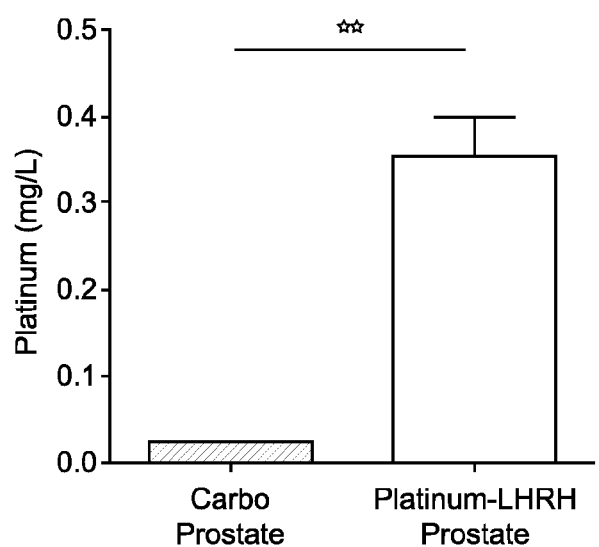
FIG. 8 compares drug uptake activity in prostate cancer cells treated with carboplatin and Pt-LHRH in accordance with the preferred embodiment of the present invention.

PC-3 Prostate Cancer cells were treated with a 100 µM concentration of carboplatin or Pt-LHRH for 24 hours. The collected samples were lysed with nitric acid and analyzed for the presence of platinum using inductive coupled plasma (ICP-OES). As shown in FIG. 8, there was a significant increase in uptake (20 fold) of Pt-LHRH compared to carboplatin.

Example 5

Migration Assay

Figure 9:
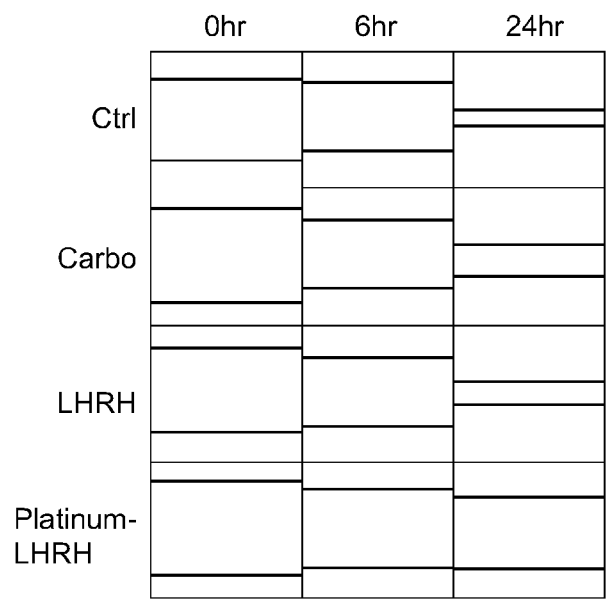
FIGS. 9A and 9B compare effects of Pt-LHRH, carboplatin and carboplatin with LHRH on breast cancer cell migration in accordance with the preferred embodiment of the present invention.
Figure 9:
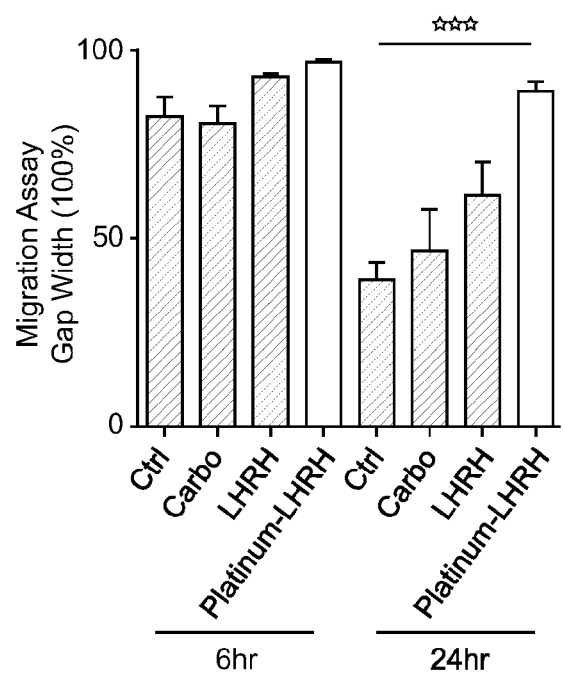

Migration of 4T1 Breast Cancer cells was examined using a scratch/wound healing assay and a transwell assay. For the scratch assay, the 4T1 cells were cultured in a 6-well plate until a confluent monolayer was formed. A 20 µl pipet tip was used to scratch the wells. The wells were sequentially rinsed with PBS and cultured in DMEM supplemented with 10% FBS. The wells were treated with PBS, carboplatin (100 µM), LHRH (100 µM), or Pt-LHRH (100 µM). Four representative 10×images were taken at 0, 6, and 24 hours and the gap width was quantified using an average of three leading edge measurements for each image. As shown in FIGS. 9A and 9B, there was a significant decrease in 4T1 cell migration during Pt-LHRH compared to carboplatin treatment. These results indicate that Pt-LHRH may be more effective at inhibiting metastasis of breast cancer cells than carboplatin alone.

Example 6

In-vivo Analysis of Impact of Pt-LHRH Conjugate on Tumor Growth

In this experiment at least one eleven week old female Balb/c mice were utilized. The animals were allowed to acclimate for 1 week before experimentation and were maintained on a 12 hours light and dark cycle, and fed standard rodent chow (Prolab ISOPRO RMH 3000 Irradiated Lab Diet; Purina Mills International). Animal protocols were approved by the committee on animal research care and use at Eastern Kentucky University. 4T1 tumors were grown in the right abdominal mammary fat pad of the mice for 7 days. After tumor initiation (~100 mm3) the mice were administered Pt-LHRH (carboplatin molar-equivalent dosage) through IP injection and compared to those treated with carboplatin (5 mg/kg/wk), no treatment, and LHRH plus carboplatin (unbound) controls for 2 weeks. Tumor growth was monitored daily and tumor volumes (mm3) were calculated using the formula: (width) 2×length/2, where width is the smaller of the two measurements. At two weeks the mice were sacrificed and tumor volume and weight were measured.

Figure 10:
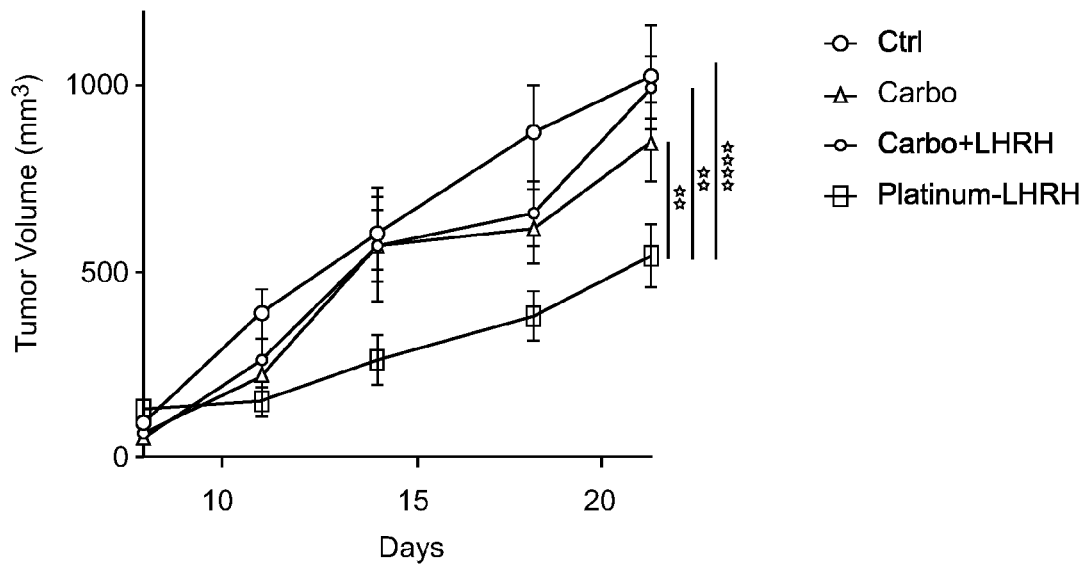
FIGS. 10A and 10B compares in-vivo effects of Pt-LHRH, carboplatin, and carboplatin with LHRH against 4T1 breast cancer cells in female BALB/c mice in accordance with the preferred embodiment of the present invention.
Figure 10:
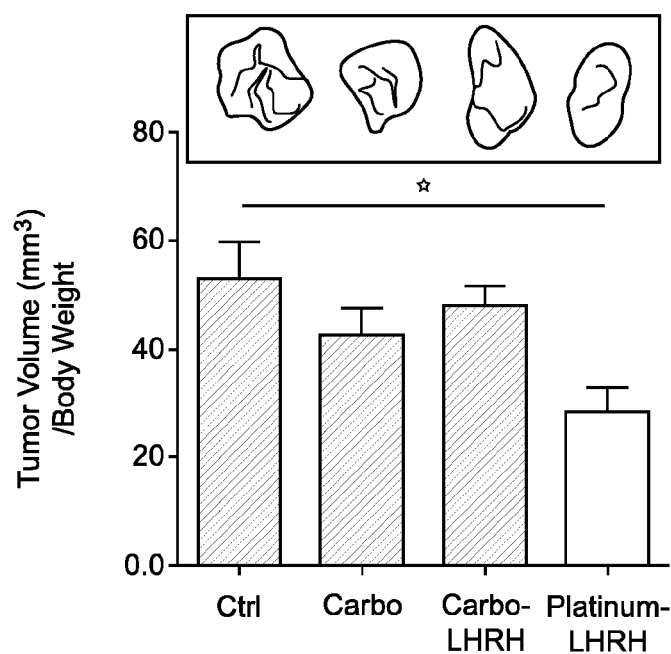
Figure 11:
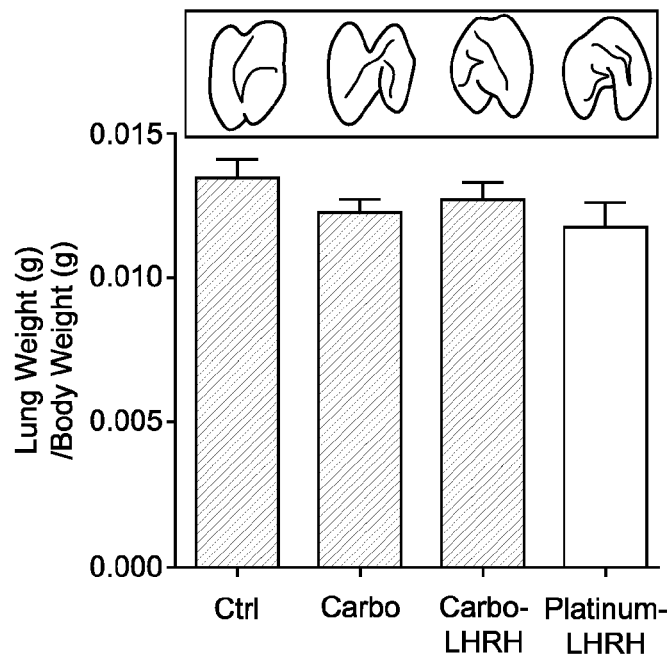
FIG. 11 compares in-vivo effects of Pt-LHRH, carboplatin, and carboplatin with LHRH on lung weight in female BALB/c mice implanted with 4T1 breast cancer cells in accordance with the preferred embodiment of the present invention.
Figure 12:
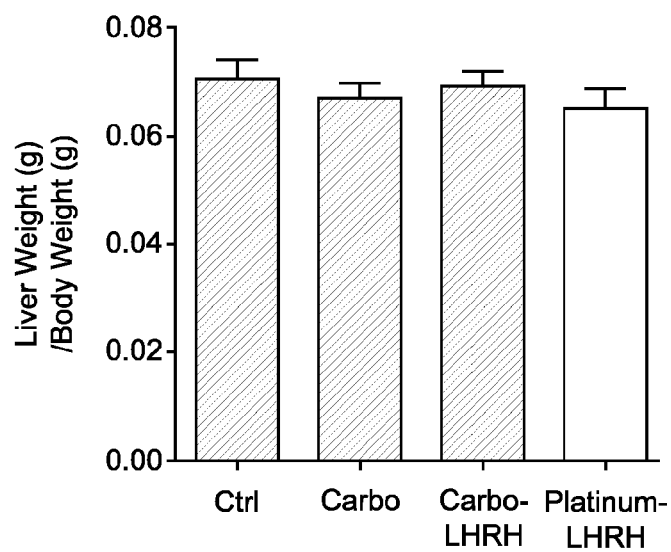
FIG. 12 compares in-vivo effects of Pt-LHRH, carboplatin, and carboplatin with LHRH on liver weight in female BALB/c mice implanted with 4T1 breast cancer cells in accordance with the preferred embodiment of the present invention.

As shown in FIGS. 10A and 10B, Pt-LHRH significantly attenuated tumor growth compared to control. Importantly at this low dose, Pt-LHRH was found therapeutically effective, whereas, no statistically significant reduction in tumor growth was found with carboplatin treatment. Previous publications highlight the use of higher treatment doses of carboplatin (ex. 25 mg/kg/wk) needed to mediate a significant therapeutic effect on tumor growth. J. M. Scalici, et al., "Imaging VCAM-1 as an indicator of treatment efficacy in metastatic ovarian cancer," J. Nucl. Med., 54 (11), pp. 1883-9 (2013); B. Das, et al., "Squalene selectively protects mouse bone marrow progenitors against cisplatin and carboplatin-induced cytotoxicity in vivo without protecting tumor growth," Neoplasia, 10 (10), pp. 1105-19 (2008); O. Karginova, et al., "Efficacy of carboplatin alone and in combination with ABT888 in intracranial murine models of BRCA-mutated and BRCA-wild-type triple-negative breast cancer," Molecular Cancer Therapeutics, 14 (4), pp. 920-30 (2015); X. M. Li, et al., "Preclinical relevance of dosing time for the therapeutic index of gemcitabine-cisplatin," British Journal of Cancer, 92 (9), pp. 1684-9 (2005). Additionally, as shown in FIG. 11, there was a slight decrease in lung weight and a significant decrease in the number of lung tumor lesions in the Pt-LHRH treated mice indicating that Pt-LHRH may attenuate breast cancer lung metastasis. Additionally, there was no difference in liver weight (see FIG. 12). Observably, there was normal locomotor activity exhibited by the mice treated with Pt-LHRH compared to the control and carboplatin treated groups. This observation may be a result from not only cancer regression, but decreased systemic toxicity (side effects).

Pt-LHRH is projected to be used in clinical settings to target reproductive cancers and any cancer type expressing the LHRH receptor in both animals and humans.

A compound that is a "conjugate" of two domains refers to a compound in which the two domains (or moieties) are covalently bonded to one another, either directly or via a linker.

Compounds used in the present invention may be administered to a patient by any "effective route". Said effective route may include oral, intrapulmonary, parenteral, subcutaneous, intramuscular, intravenous, intra-arterial, intrathecal, transdermal, and via mucous membrane (nasal, sublingual, rectal, urinary, and reproductive tract). Parenteral infusions can include intraperitoneal administration. The compounds are capable of transdermal delivery in the form of a slow-release subcutaneous implant.

Compounds used in the present invention may be administered by any pharmaceutically acceptable carrier preparations. The carriers and preparations may include sterile, aqueous or non-aqueous solutions, suspensions, and emulsions. Compounds may be administered in combination with a slow-release mechanism. Examples of non-aqueous solvents are propylene glycol, polyethylene glycol, vegetable oils, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. The active therapeutic ingredient may be mixed with excipients that are pharmaceutically acceptable and are compatible with the active ingredient. Suitable excipients include water, saline, dextrose, glycerol and ethanol, or combinations thereof. Intravenous vehicles include fluid and nutrient replenishers, electrolyte replenishers, such as those based on Ringer's dextrose, and the like. Preservatives and other additives may also be present such as antimicrobials, anti-oxidants, chelating agents, inert gases, and the like.

The form may vary depending upon the route of administration. For example, compositions for injection may be provided in the form of an ampoule, each containing a unit dose amount, or in the form of a container containing multiple doses.

A compound in accordance with the present invention may be formulated into therapeutic compositions as pharmaceutically acceptable salts. These salts include acid addition salts formed with inorganic acids, for example hydrochloric or phosphoric acid, or organic acids, such as acetic oxalic, or tartaric acid and the like. Salts also include those formed from inorganic bases such as sodium, potassium, ammonium, calcium or ferric hydroxides, and organic bases such as isopropylamine, trimethylamine, histidine, procaine and the like.

As used herein, an "effective amount" of a compound is an amount that when administered to a patient inhibits or reduces the growth of targeted tumors to a clinically significant degree; or alternatively, to a statistically significant degree as compared to control.

As used herein, a "platinum drug" is a chemotherapeutic agent in the platinum family and includes carboplatin, cisplatin, oxaliplatin and any derivatives thereof. A platinum drug may also refer to the Pt group metal, alone.

As used herein, a "linker" refers to any linkers or combination of linkers known in the art including acetate linkers, PEG groups or variations in carbon length chains, ester linkers, sugars, lectins, antibodies and their fragments, hormones and hormone analogues.

As used herein, an "analog" is a molecule comprised of a peptide sequence that is comparable to the endogenously produced compound, in which, one or more residues have been replaced, deleted or modified with an alternate desired moiety. An analog of LHRH can be a natural or a synthetic peptide that resembles LHRH in structure and/or function.

All the references cited in this disclosure are hereby incorporated by reference in their entirety.

The foregoing description of several embodiments of the Pt-LHRH conjugate and treatment methods utilizing the Pt-LHRH conjugate has been presented for purposes of illustration. It is not intended to be exhaustive or to limit the application to the precise forms disclosed, and obviously, many modifications and variations are possible in light of the above teaching. It is understood that the invention may be applied in ways other than as specifically set forth herein without departing from the scope of the invention.

This application incorporates by reference the sequence listing submitted electronically as an ASCII text file on Apr. 2, 2018, titled "Sequence Listing LHRH Platinum Conjugates," which was submitted with U.S. patent application Ser. No. 15/367,428 filed Dec. 2, 2016, and incorporated by reference herein.

What is claimed is:

1. A method for delivering a cytotoxic chemotherapeutic agent to a cell that expresses a lutenizing hormone releasing hormone (LHRH) receptor comprising administering to the cell a compound comprised of:
   a LHRH or analog thereof;
   a cytotoxic platinum chemotherapeutic agent; and
   a linker, wherein the linker comprises malonate;
   wherein the LHRH or analog thereof is covalently bonded to the cytotoxic platinum chemotherapeutic agent utilizing the linker and further wherein the LHRH analog is selected from the group consisting of [DLys6]-LHRH, [D-Trp6]-LHRH, [D-Ala6]-LHRH, [Gln8]-LHRH, antide, gonadorelin, leuprolide, leuprorelin, histerlin, buserelin, or triptorelin.

2. The method of claim 1, wherein the cell is a cancer cell.

3. The method of claim 2, wherein the cancer cell is a prostate cell or a breast cell.

4. The method of claim 2, wherein the cell is in vivo.

5. The method of claim 1, wherein the compound is administered via oral, intrapulmonary, parenteral, subcutaneous, intramuscular, intravenous, intra-arterial, intrathecal, transdermal, or mucous membrane route.

6. The method of claim 1, wherein the compound is administered intravenously.

7. The method of claim 1, wherein the compound further comprises at least one of a pharmaceutically acceptable carrier, an excipient, a vehicle, or a combination thereof.

8. The method of claim 1, wherein the linker further comprises a polyethylene glycol (PEG) group.

9. The method of claim 1, wherein the linker comprises malonate and an additional carbon.

10. The method of claim 1, wherein the linker further comprises an additional carbon.

11. The method of claim 1, wherein the cytotoxic platinum chemotherapeutic agent comprises cisplatin.

12. The method of claim 1, wherein the cytotoxic platinum chemotherapeutic agent comprises carboplatin.

13. The method of claim 1, wherein the LHRH comprises the amino acid sequence as set forth in SEQ ID NO: 2.

14. The method of claim 1, wherein the LHRH comprises the amino acid sequence as set forth in SEQ ID NO: 1.

15. The method of claim 1, wherein the linker does not include a polyethylene glycol (PEG) group.

16. The method of claim 1, wherein the LHRH comprises an amino terminal pyroglutamic acid.

17. A method for delivering a cytotoxic chemotherapeutic agent to cells in a subject that express lutenizing hormone releasing hormone (LHRH) receptor, the method comprising administering to a subject a compound comprised of:
 a LHRH or analog thereof;
 a cytotoxic platinum chemotherapeutic agent; and
 a linker, wherein the linker comprises malonate;
 wherein the LHRH or analog thereof is covalently bonded to the cytotoxic platinum chemotherapeutic agent utilizing the linker and further wherein the LHRH analog is selected from the group consisting of [DLys6]-LHRH, [D-Trp6]-LHRH, [D-Ala6]-LHRH, [Gln8]-LHRH, antide, gonadorelin, leuprolide, leuprorelin, histerlin, buserelin, or triptorelin.

\* \* \* \* \*

SEQUENCE LISTING

```
<160> NUMBER OF SEQ ID NOS: 2

<210> SEQ ID NO 1
<211> LENGTH: 10
<212> TYPE: PRT
<213> ORGANISM: Homo sapiens
<220> FEATURE:
<221> NAME/KEY: MOD_RES
<222> LOCATION: (1)..(10)
<223> OTHER INFORMATION: Xaa in position 1 is pyroGlu. Luteinizing
      hormone releasing hormone (LHRH)

<400> SEQUENCE: 1

Xaa His Trp Ser Tyr Gly Leu Arg Pro Gly
1               5                   10

<210> SEQ ID NO 2
<211> LENGTH: 10
<212> TYPE: PRT
<213> ORGANISM: Homo sapiens
<220> FEATURE:
<221> NAME/KEY: MOD_RES
<222> LOCATION: (1)..(10)
<223> OTHER INFORMATION: Xaa in position 1 is pyroGlu. Xaa in position 6
      is D-Lys. Luteinizing hormone releasing hormone (LHRH)

<400> SEQUENCE: 2

Xaa His Trp Ser Tyr Xaa Leu Arg Pro Gly
1               5                   10
```